United States Patent
Qin et al.

(10) Patent No.: US 9,765,305 B2
(45) Date of Patent: Sep. 19, 2017

(54) MUTANT VACCINIA VIRUS STRAINS, USES THEREOF AND METHOD OF PRODUCING THE SAME

(71) Applicant: TOT SHANGHAI R&D CENTER CO., LTD., Shanghai (CN)

(72) Inventors: Li Qin, Alberta (CA); Min Liang, Shanghai (CN); David H. Evans, Alberta (CA)

(73) Assignee: TOT SHANGHAI R&D CENTER CO., LTD., Shanghai (CN)

( * ) Notice: Subject to any disclaimer, the term of this patent is extended or adjusted under 35 U.S.C. 154(b) by 63 days.

(21) Appl. No.: 14/863,330

(22) Filed: Sep. 23, 2015

(65) Prior Publication Data
US 2016/0010064 A1   Jan. 14, 2016

Related U.S. Application Data

(63) Continuation of application No. PCT/CN2013/074028, filed on Apr. 10, 2013.

(51) Int. Cl.
*C12N 7/00* (2006.01)
*C07K 14/005* (2006.01)
*A61K 48/00* (2006.01)

(52) U.S. Cl.
CPC .............. *C12N 7/00* (2013.01); *C07K 14/005* (2013.01); *A61K 48/00* (2013.01); *C12N 2710/24121* (2013.01); *C12N 2710/24132* (2013.01); *C12N 2710/24143* (2013.01)

(58) Field of Classification Search
None
See application file for complete search history.

(56) References Cited

U.S. PATENT DOCUMENTS

2013/0071430 A1   3/2013   Nakamura et al.

FOREIGN PATENT DOCUMENTS

| CN | 101671695 A | 3/2010 |
|---|---|---|
| WO | 2007030668 A2 | 3/2007 |
| WO | 2011125469 A1 | 10/2011 |
| WO | 2012142529 A2 | 10/2012 |

OTHER PUBLICATIONS

Guo et al. Vaccinia as a vector for gene delivery. Expert Opin Biol Ther. Jun. 2004;4(6):901-17.*
Li et al. Structure function studies of vaccinia virus host range protein k1 reveal a novel functional surface for ankyrin repeat proteins. J Virol. Apr. 2010;84(7):3331-8.*
International Search Report of PCT Application No. PCT/CN2013/074028, mailed Jan. 23, 2014.
Afonso, C.L., et al., The Genome of Fowlpox Virus, Journal of Virology, 2000, vol. 74, No. 8, pp. 3815-3831.
Guo, Z.S., et al., Oncolytic Virotherapy: Molecular Targets in Tumor-Selective Replication and Carrier Cel-Mediated Delivery of Oncolytic Viruses, Biochim Biophys Acta., NIH Public Access Author Manuscript, available in PMC Jun. 21, 2010, pp. 1-32.
Guo, Z.S. et al. "Oncolytic Virotherapy: Molecular Targets in Tumor-Selective Replication and Carrier Cell-Mediated Delivery of Oncolytic Viruses", Biochim Biophys Acta. vol. 1785, Apr. 2008, pp. 217-231.
Zhao, L. et al. "Immunogenicity in mice and rhesus monkeys vaccinated with recombinant vaccinia virus expressing bivalent E7E6 fusion proteins from human papillomavirus types 16 and 18", Virology Journal20118:302, Jun. 15, 2011, 12 pages.
Steve H Thorne et al:"Rational strain selection and engineering creates a broad-spectrum, systemically effective oncolytic poxvirus, JX-963", Journal of Clinical Investigation, American Society for Clinical Investigation, US, vol. 117, No. 11,Nov. 1, 2007, pp. 3350-3358.
S Chalikonda et al:"Oncolytic virotherapy for ovarian carcinomatosis using a replication-selective vacciniavirus armed with a yeast cytosine deaminase gene", Cancer Gene Therypy, vol. 15. No. 2, Dec. 14, 2007, pp. 115-125.
S Yang et al:"A new recombinant vaccinia with targeted deletion of three viral genes: its safety and efficacy as an oncolytic virus", Gene Therapy, vol. 14, No. 8, Feb. 1, 2007, pp. 638-647.
Z.S.Guo:"The Enhanced Tumor Selectivity of an Oncolytic Vaccinia Lacking the Host Range and Antiapoptosis Genes SPI-1 and SPI-2", Cancer Research, vol. 65, No. 21, Nov. 1, 2005, pp. 9991-9998.
Meng, X. et al., "Vaccinia virus K1L protein supports viral replication in human and rabbit cells through a cell-type-specific set of its ankyrin repeat residues that are distinct from its binding site for ACAP", Virology, 353/1, Sep. 15, 2006,pp. 220-233.
Supplementary European Search Report issued on Nov. 2, 2016 for counterpart European patent application No. 13881492.6.

* cited by examiner

*Primary Examiner* — Michelle S Horning
(74) *Attorney, Agent, or Firm* — Perkins Coie LLP; Viola T. Kung

(57) ABSTRACT

The present disclosure provides mutant vaccinia virus strains that can selectively replicate in tumor cells. The present disclosure also provides use of the mutant vaccinia virus strains for preventing and treating tumors.

7 Claims, 6 Drawing Sheets

Genes located in a 5.7 kbp deletion in TianTan clone TP03 terminal inverted repeats

| Gene function or feature | Copenhagen Gene number | TianTan TP05 Gene number | TianTan TP05 Size (bp) | TP03 Size (bp) |
|---|---|---|---|---|
| Ankyrin | C17L/B23R | TT_005 | 528 | 0 |
| Unknown | C16L/B22R | TT_006 | 546 | 0 |
| Unknown | C15L/B21R | TT_007 | 264 | 0 |
| Unknown | - | TT_008 | 156 | 0 |
| Unknown | C14L | TT_009 | 573 | 0 |
| Serpin (SPI-1) | C12L | TT_010 | 1062 | 0 |
| Vaccinia growth factor | C11R | TT_011 | 426 | 253[1] |

[1] C-terminal fragment

Figure 6

MUTANT VACCINIA VIRUS STRAINS, USES THEREOF AND METHOD OF PRODUCING THE SAME

This application is a continuation of International Application PCT/CN2013/074028, filed Apr. 10, 2013, published Oct. 16, 2014, under PCT Article 21(2) in English. The contents of the above application are incorporated herein by reference in its entirety.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing.txt with a creation date of Aug. 13, 2015, and a size of 922 bytes. The Sequence Listing filed via EFS-Web is part of the specification and is hereby incorporated in its entirety by reference herein.

FIELD OF THE INVENTION

This disclosure relates to novel mutant vaccinia virus strains, uses thereof and methods of producing the same.

BACKGROUND

Gene therapy has drawn lots of attention in the studies for cancer treatment. The efficiency of transduction and expression of therapeutic genes in tumor cells are critical for gene therapy methods. Various approaches have been developed for improving the efficiencies of gene transduction and expression in tumor cells. Various viruses have been studied and tested for their potential to be used as vectors for carrying genes of interests to tumor cells. However, the safety and selectivity of a viral vector for tumor cells are major issues of concern when selecting viral vectors as candidates for gene therapy.

Vaccinia virus is closely related to the virus that causes smallpox and has been used as a live vaccine in the smallpox eradication program. It has recently become a subject of study as a vector for carrying and delivering genes of interests to a subject under treatment in gene therapy.

Vaccinia virus contains two copies of the vaccinia growth factor (VGF) genes which are located in the inverted terminal repetition (ITR) of the vaccinia virus genome. The VGF protein is a highly glycosylated 77-residue epidermal growth factor (EGF)-like polypeptide. The VGF protein is expressed and secreted early in viral infection and acts as a mitogen to prime surrounding cells for vaccinia infection and has been shown to play a critical role in vaccinia virus infection (Buller et al. J. Virol. 62 (1988): 866-74).

Vaccinia virus also contains Serpin genes and Ankyrin genes. Serpin genes are a family of genes that encode serine protease inhibitors. Serpins are potentially involved in multiple biological functions such as regulation of coagulation, fibrinolysis, immune response, inflammation, tumor invasion and apoptosis (see Kummer et al. Methods 32 (2004): 141-9). Ankyrin genes encode a family of proteins that possess binding sites for different integral membrane proteins and play a critical role in biological process involving protein-protein interaction (see Li et al. Biochemistry 45 (2006): 15168-78).

SUMMARY OF THE INVENTION

In one aspect, the present disclosure relates to a mutant vaccinia virus strain that can selectively replicate in tumor cells. In certain embodiments, the mutant virus strain has decreased virulence.

In another aspect, the present disclosure provides a mutant vaccinia virus strain, wherein the encoding sequences of the VGF genes in the genome of the virus are truncated in whole or in part.

In another aspect, the present disclosure provides a mutant vaccinia virus strain, wherein the encoding sequences of the Serpin genes in the genome of the virus are truncated in whole or in part.

In another aspect, the present disclosure provides a mutant vaccinia virus strain, wherein the encoding sequences of the Ankyrin genes in the genome of the virus are truncated in whole or in part.

In another aspect, the present disclosure provides a method of producing a mutant vaccinia virus strain, which includes truncating the encoding sequences of the VGF genes completely or partially from the virus genome so that the virus cannot express functionally active VGF proteins. In certain embodiments, the method includes truncating the encoding sequences of the VGF genes, the Serpin genes and the Ankyrin genes completely or partially from the virus genome so that the virus cannot express functionally active VGF proteins, Serpin proteins and Ankyrin proteins.

In another aspect, the present disclosure provides uses of a mutant vaccinia virus as a vector for selectively delivering a target gene to a tumor cell and expressing the target gene in the tumor cell.

In another aspect, the present disclosure provides a method for producing a recombinant gene product, which comprises inserting a target gene into the genome of a mutant vaccinia virus of the present disclosure. In another aspect, the present disclosure provides a recombinant gene product comprising the nucleic acid sequences of a mutant vaccinia virus described herein and the nucleic acid sequences of a target gene.

BRIEF DESCRIPTION OF THE DRAWINGS

FIG. 3A shows the binding sites of the PCR primers to the TP03 and TP05 left telomere regions. FIG. 3B shows the PCR results of TP03, TP05, TP11, TP12, TP13, TP18, TP05 and the pool (unpurified stock of viruses) using TT010F and TT011R, or TT004F and TT011R as primer pairs, respectively. FIG. 3C shows the Southern blot results of ScaI digested DNAs encoding the left and right TIRs in TP03, TP11, TP05, TP13 and the pool.

FIG. 6 shows a table listing the genes located in a 5.7 kbp fragment in the terminal inverted repeats of the TP05 type virus while the 5.7 kbp fragment is missing from the TP03 type virus.

DETAILED DESCRIPTION OF THE INVENTION

Mutant Vaccinia Virus Strains

Figure 1:
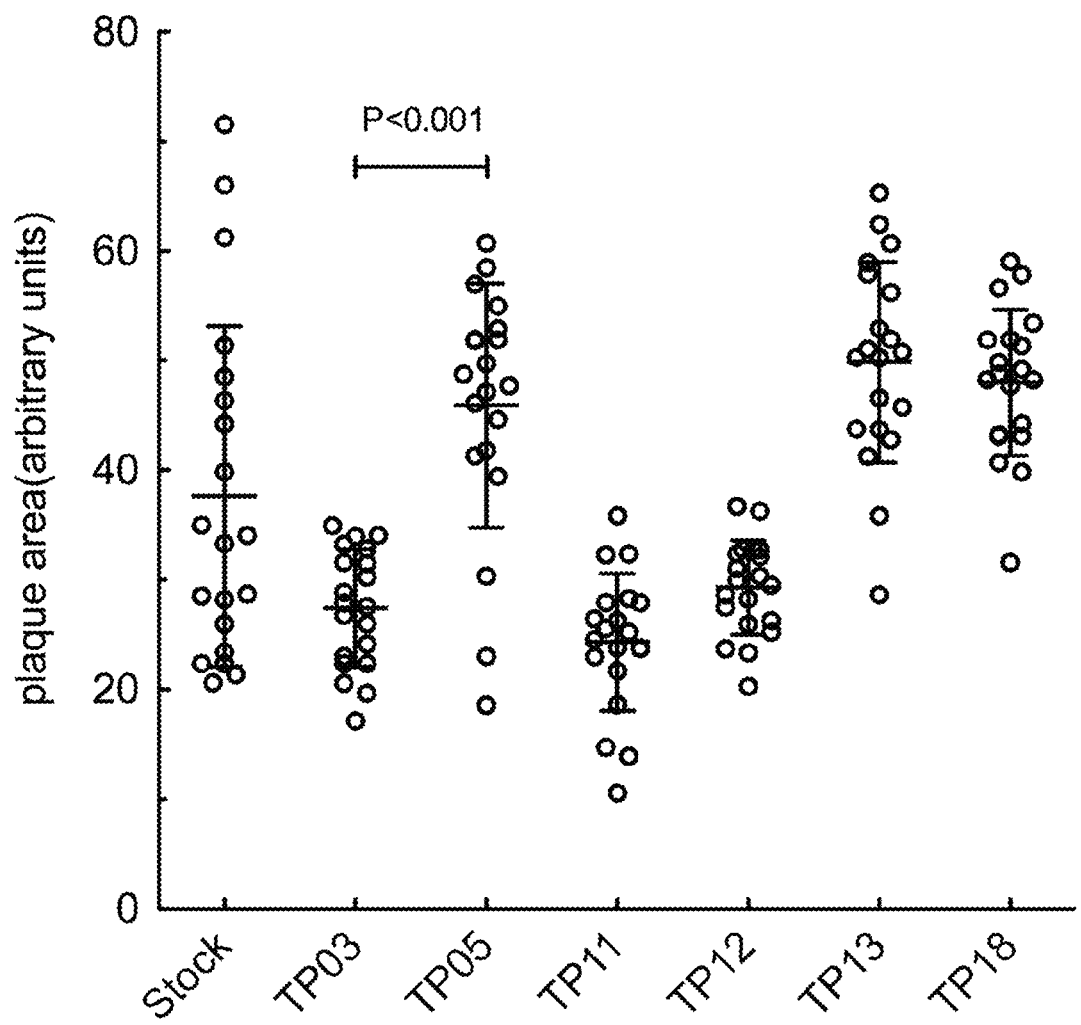
FIG. 1 shows plaques formed by viruses cloned from a stock of vaccinia virus strain TianTan. Each of the plaque-purified viruses were separately plated on BSC-40 cells, cultured for two days, fixed, stained with crystal violet, and photographed. ImageJ (Schneider et al. Nat. Methods 9 (2012): 671-5) was then used to measure the area sizes of 20 plaques randomly selected from each dish for each virus clone. The original stock appears to contain a mix of both large plaques and small plaques. The plaque-purified viruses were separated into two groups, of which, one group (e.g. TP03, TP11 and TP12) generates smaller plaques, and the other group (e.g. TP05, TP13 and TP18) generates larger plaques. The difference between the plaque sizes of the two groups are statistically significant (P<0.001).
Figure 2:
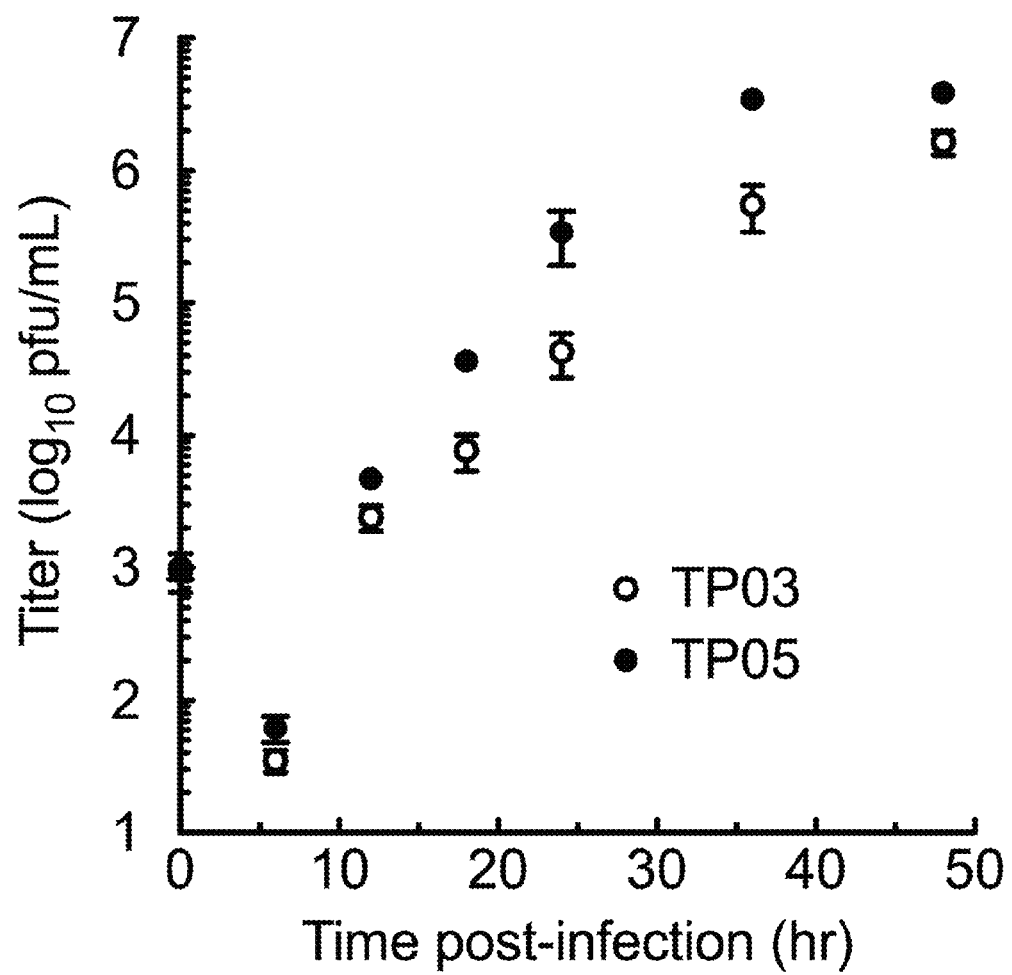
FIG. 2 shows the titers of the TP03 type vaccinia virus and the TP05 type vaccinia virus after infection with BSC-40 cells. BSC-40 cells were respectively infected with the TP03 and TP05 viruses at the multiplicity of infection (MOI) of 0.01 (i.e. MOI=0.01), incubated at 37° C., harvested by freeze-thaw, and the yield of virus determined by titration on BSC-40 cells. The TP03 viruses grow more slowly, and to lower titers, than the TP05 viruses. The growth rate difference between the two strains is statistically significant (P<0.01).

The inventors of the present disclosure have identified and isolated a mutant vaccinia virus strain with enhanced safety and tumor selectivity from the vaccinia virus strain TianTan. The inventors found that the TianTan strain vaccinia virus produced plaques with various area sizes when cultured on monkey kidney BSC-40 cells. The plaques can be generally divided into two types, one type has an area size significantly smaller than the other. Through cloning and screening, the inventors were able to separate the viruses into two strains, one is the TP03 type which has a smaller plaque area size, and the other is the TP05 type which has a larger plaque area size. In certain embodiments, the TP03 type has plaques with an area size that is about half of the area size of the plaques of the TP05 type (FIG. 1). In certain embodiments, the size of the small plaques formed by the TP03 type vaccinia virus can be less than about 30%, about 35%, about 40%, about 45%, about 50%, about 55%, about 60%, about 65%, about 70%, about 75%, or about 80% of that of the large plaques of the TP05 type vaccinia virus. The area size of a plaque can be determined by measuring the mean radius, diameter, or area of the plaque formed by the virus as described in U.S. Pat. No. 4,213,965, U.S. Pat. No. 5,690,940 and U.S. Pat. No. 7,037,508.

It was also found that the TP03 type has a lower multiplicity of infection on non-dividing host cells than the TP05 type. In certain embodiments, the multiplicity of infection of the TP03 type is less than about 90%, about 80%, about 70%, about 60%, or about 50% of the multiplicity of infection of the TP05 type (FIG. 2). The lower multiplicity of infection can be indicative of decreased virulence. The multiplicity of infection of a virus may be determined by measuring the viral titers or immunohistochemistry results of cells or tissues infected with the virus. A decrease in the viral titers or improved immunohistochemistry results can be indicative of a decrease in virulence. Detailed description of virulence evaluation can be found in U.S. Pat. No. 7,740,867 and U.S. Pat. No. 7,732,188.

Furthermore, the virulence of a virus can be evaluated by other methods commonly used in the art, for example, animal survival or host cell growth study. For animal survival study, the viruses can be injected into animals and the percentage of animals surviving after infection with different viruses will be recorded to generate a survival curve and/or determine the $LD_{50}$. A virus that results in a higher survival rate or longer survival time or higher $LD_{50}$ may be considered to have decreased virulence and therefore enhanced safety.

The gene sequences of the TP03 type and TP05 type viruses were determined using standard sequencing method known in the art (see, for example, Qin et al. J. Virol. 85 (2011): 13049-60; Chen et al. Virology 317 (2003): 165-86.). The sequencing results revealed that the TP03 type is a mutant strain that contains large deletions in the genome of the virus while the TP05 type contains a nearly complete genome of a vaccinia virus that is representative of the original TianTan virus strain. FIGS. 4 and 5 show schematic diagrams of the left telomere and right telomere of the TP03 type and TPO5 type viruses. The gene deletion of the TP03 type is a symmetrical 5.7 kbp deletion in the left and right telomeric inverted repeats (TIRs) of the virus, in which the promoters and N-termini of both copies of the VGF genes are deleted, the Serpin (SPI-1) gene, Ankyrin gene and certain other genes are also deleted. The gene deletions in the TP03 type viruses and the corresponding homologous genes in the TP05 type viruses are listed in a Table shown in FIG. 6.

The TP03 type virus strain was deposited on Apr. 8, 2013 with the China Center for Type Culture Collection (CCTCC) under CCTCC deposit number v201307, under the Budapest Treaty provisions.

In another aspect, the present disclosure also provides a recombinant mutant vaccinia virus with the VGF genes artificially truncated so that the virus expresses no functionally active VGF proteins. The term “functionally active,” when used with respect to a molecule such as a protein, means that the molecule is capable of performing at least one function or activity at its active state. The function or activity refers to, for example, but not limited to biological, physiological, immunological function or activity.

In certain embodiments, both VGF genes in the genome of the vaccinia virus are completely or partially truncated, for example, more than 99%, more than 98%, more than 95%, more than 90%, more than 85%, more than 80%, more than 75%, more than 70%, more than 65%, more than 60%, more than 55%, more than 50%, more than 45%, more than 40%, more than 35%, more than 30%, more than 25%, more than 20%, more than 15%, more than 10% of the VGF genes are truncated. In a preferred embodiment, both VGF genes are completely truncated. In certain embodiments, the VGF genes are truncated by deletions of at least 10, 15, 20, 25, 30, 35, 40, 45, 50, 55, 60, 65, 70, 75, 80, 85, 90, 95, 100, 150, 200 or more contiguous nucleotides in each VGF gene, either contiguous or discontiguous.

In another aspect, the present disclosure also provides a recombinant mutant vaccinia virus with the Serpin genes artificially truncated so that the virus cannot express functionally active Serpin proteins. In certain embodiments, the Serpin genes in the genome of the vaccinia virus are completely or partially truncated, for example, more than 99%, more than 98%, more than 95%, more than 90%, more than 85%, more than 80%, more than 75%, more than 70%, more than 65%, more than 60%, more than 55%, more than 50%, more than 45%, more than 40%, more than 35%, more than 30%, more than 25%, more than 20%, more than 15%, more than 10% of the Serpin gene is truncated. In a preferred embodiment, the Serpin genes are completely truncated. In certain embodiments, the Serpin genes are truncated by deletions of at least 10, 15, 20, 25, 30, 35, 40, 45, 50, 55, 60, 65, 70, 75, 80, 85, 90, 95, 100, 150, 200, 300, 400, 500, 700, 900 or more contiguous nucleotides in each Serpin gene, either contiguous or discontiguous.

In another aspect, the present disclosure also provides a recombinant mutant vaccinia virus with the Ankyrin genes artificially truncated so that the virus cannot express functionally active Ankyrin proteins. In certain embodiments, the Ankyrin genes in the genome of the vaccinia virus are completely or partially truncated, for example, more than 99%, more than 98%, more than 95%, more than 90%, more than 85%, more than 80%, more than 75%, more than 70%, more than 65%, more than 60%, more than 55%, more than 50%, more than 45%, more than 40%, more than 35%, more than 30%, more than 25%, more than 20%, more than 15%, more than 10% of the Ankyrin gene is truncated. In a preferred embodiment, the Ankyrin genes are completely truncated. In certain embodiments, the Ankyrin genes are truncated by deletions of at least 10, 15, 20, 25, 30, 35, 40, 45, 50, 55, 60, 65, 70, 75, 80, 85, 90, 95, 100, 150, 200, 300, 400 or more contiguous nucleotides in each Ankyrin gene, either contiguous or discontiguous.

In another aspect, the present disclosure provides a recombinant mutant vaccinia virus with the VGF genes and the Serpin genes artificially truncated so that the virus cannot express functionally active VGF proteins and Serpin proteins. In certain embodiments, the VGF genes and the Serpin genes in the genome of the vaccinia virus are completely or partially truncated, for example, more than 99%, more than 98%, more than 95%, more than 90%, more than 85%, more than 80%, more than 75%, more than 70%, more than 65%, more than 60%, more than 55%, more than 50%, more than 45%, more than 40%, more than 35%, more than 30%, more than 25%, more than 20%, more than 15%, more than 10% of each of the VGF and the Serpin genes are truncated. In a preferred embodiment, all of the VGF genes and Serpin genes in the vaccinia virus genome are completely truncated.

In another aspect, the present disclosure provides a recombinant mutant vaccinia virus with the VGF genes and the Ankyrin genes artificially truncated so that the virus cannot express functionally active VGF proteins and Ankyrin proteins. In certain embodiments, the VGF genes and the Ankyrin genes in the genome of the vaccinia virus are completely or partially truncated, for example, more than 99%, more than 98%, more than 95%, more than 90%, more than 85%, more than 80%, more than 75%, more than 70%, more than 65%, more than 60%, more than 55%, more than 50%, more than 45%, more than 40%, more than 35%, more than 30%, more than 25%, more than 20%, more than 15%, more than 10% of each of the VGF and the Ankyrin genes are truncated. In a preferred embodiment, all of the VGF genes and Ankyrin genes in the vaccinia virus genome are completely truncated.

In another aspect, the present disclosure provides a recombinant mutant vaccinia virus with the Ankyrin genes and the Serpin genes artificially truncated so that the virus cannot express functionally active Ankyrin proteins and Serpin proteins. In certain embodiments, the Ankyrin genes and the Serpin genes in the genome of the vaccinia virus are completely or partially truncated, for example, more than 99%, more than 98%, more than 95%, more than 90%, more than 85%, more than 80%, more than 75%, more than 70%, more than 65%, more than 60%, more than 55%, more than 50%, more than 45%, more than 40%, more than 35%, more than 30%, more than 25%, more than 20%, more than 15%, more than 10% of each of the Ankyrin and the Serpin genes are truncated. In a preferred embodiment, all of the Ankyrin genes and Serpin genes in the vaccinia virus genome are completely truncated.

In another aspect, the present disclosure provides a recombinant mutant vaccinia virus with the VGF genes, the Serpin genes and the Ankyrin genes artificially truncated so that the virus cannot express functionally active VGF, Serpin and Ankyrin proteins. In certain embodiments, the VGF genes, the Serpin genes and the Ankyrin genes in the genome of the vaccinia virus are completely or partially truncated, for example, more than 99%, more than 98%, more than 95%, more than 90%, more than 85%, more than 80%, more than 75%, more than 70%, more than 65%, more than 60%, more than 55%, more than 50%, more than 45%, more than 40%, more than 35%, more than 30%, more than 25%, more than 20%, more than 15%, more than 10% of each of the VGF genes, the Serpin genes and the Ankyrin genes are truncated. In a preferred embodiment, all of the VGF genes, Serpin genes, and Ankyrin genes in the vaccinia virus genome are completely truncated.

Gene truncation in the virus genome can be produced by various methods known in the art, for example, homologous recombination. Homologous recombination is a type of genetic recombination in which nucleotide sequences are exchanged between two similar or identical nucleic acid molecules. Homologous recombination can be conducted by the steps of first creating a vaccinia shuttle plasmid containing a reporter gene for homologous recombination into the target region, infecting a suitable host cell with a native vaccinia virus, transfecting the native vaccinia virus with the vaccinia shuttle plasmid to allow homologous recombination of the shuttle plasmid into the target region, and isolating the positive plaques according to the reporter gene product. The method to design a vaccinia virus shuttle vector is known in the art, as described by Du et al. J. Virol. Methods 185 (2012): 175-83; Blasco et al. Gene 158 (1995): 157-62; Coupar et al. Gene 68 (1988): 1-10; Falkner et al. J Virol. 64 (1990): 3108-11.

In another aspect, the present disclosure relates to a method of producing a mutant vaccinia virus strain, which includes truncating the encoding sequences of the VGF genes completely or partially from the virus genome so that the virus cannot express functionally active VGF proteins. In certain embodiments, the method further includes truncating the encoding sequences of the Serpin genes completely or partially from the virus genome so that the virus cannot express functionally active Serpin proteins. In certain embodiments, the method further includes truncating the encoding sequences of the Ankyrin genes completely or partially from the virus genome so that the virus cannot express functionally active Ankyrin proteins. In certain embodiments, the method includes truncating the encoding sequences of the VGF genes, the Serpin genes and the Ankyrin genes completely or partially from the virus genome so that the virus cannot express functionally active VGF proteins, Serpin proteins and Ankyrin proteins.

Vaccinia virus includes, but not limited to, Western Reserve (WR), Copenhagen, Tashkent, TianTan, Lister, Wyeth (also known as Dryvax), 1HD-J, and IHD-W, Brighton, Ankara, MVA, Dairen I, LIPV, LC16M8, LC16MO, LIVP, WR 65-16, and Connaught.

Uses of the Mutant Virus Strains

The mutant vaccinia viruses described herein can selectively replicate in tumor cells and can be useful for selectively infecting tumor cells. As used herein, "selectively replicate" means that the replication rate of the mutant virus in one type of cells (e.g. tumor cells) is significantly higher than that in another type of cells (e.g. normal cells). In certain embodiments, a mutant vaccinia virus shows at least 1 fold, 2 folds, 3 folds, 4 folds, 5 folds, 10 folds, 50 folds, 100 folds or 1000 folds higher multiplicity of infection in tumor cells than in normal cells. In certain embodiments, the mutant vaccinia virus shows at least 50%, 60%, 70%, 80% or 90% higher multiplicity of infection in tumor cells than in normal cells.

In certain embodiments, the mutant vaccinia viruses of the present disclosure can selectively replicate in liver cancer cells (e.g. Hepal-6 cells, Hep3B cells, 7402 cells, and 7721 cells), breast cancer cells (e.g. MCF-7 cells), Tongue cancer cells (e.g. TCa8113 cells), adenoid cystic cancer cell (e.g. ACC-M cells), prostate cancer cells (e.g. LNCaP cells), human embryo kidney cell (e.g. HEK293 cells), lung cancer cell (e.g. A549 cells), and cervical cancer cell (e.g. Hela cells).

In another aspect, the mutant vaccinia viruses of the present disclosure have decreased virulence to normal cells. In certain embodiments, the mutant vaccinia viruses show less than 70%, 60%, 50%, 40%, 30%, 20%, 10% of the multiplicity of infection in normal cells than the wild type vaccinia virus.

In another aspect, a mutant vaccinia virus described herein can be used as a vector for selectively delivering a target gene to a tumor cell and expressing the target gene in the tumor cell. The term "express" as used herein refers to a process wherein a DNA sequence is read by a RNA polymerase to produce a RNA chain complementary to the DNA sequence, and/or a process wherein a RNA sequence is read by a ribosome to produce a peptide encoded by the DNA sequence and the RNA sequence.

In another aspect, the present disclosure provides a method for producing a recombinant gene product, which comprises inserting a target gene into the genome of a mutant vaccinia virus of the present disclosure. In another aspect, the present disclosure provides a recombinant gene product comprising the nucleic acid sequences of a mutant vaccinia virus described herein and the nucleic acid sequences of a target gene.

In certain embodiments, such target genes may include, without limitation, genes that can kill or inhibit tumor cells, genes that can enhance immune responses against tumor cells, genes that can repair or replace mutated or altered genes of tumor cells, or genes that can make tumor cells more sensitive to chemotherapy or radiation therapy. In certain embodiments, the target genes are cytokins such as colony-stimulating factors (e.g. granulocyte macrophage colony-stimulating factors (GM-CSFs), macrophage-colony stimulating factors (M-CSFs), granulocyte-colony stimulating factors (G-CSFs)), stem cell factors, erythropoietin, interferons (IFNs), tumor necrosis factors (TNFs) and chemokines. In certain embodiments, the target genes encode for antigen presenting polypeptides such as heat shock proteins. In certain embodiments, the target genes encode for monoclonal antibodies against proteins that may be associated with tumors, for example, monoclonal antibodies against the vascular endothelial growth factors or the tumor necrosis factors.

A target gene may be inserted into the mutant vaccinia viruses using conventional methods known in the art. For example, the target gene may be produced by polymerase chain reaction (PCR) and carry specific enzymatic sites on each end of the target gene, which enzymatic sites are complementary to the same or similar enzymatic sites on the mutant vaccinia virus, and the target gene is ligated with the virus through binding at the enzymatic sites. For more details, see, for example, Sambrook et al. Molecular Cloning: A Laboratory Manual (Cold Spring Harbor Laboratory, N.Y. (1989)), which is incorporated herein by reference in its entirety.

In another aspect, a mutant vaccinia virus of the present disclosure and a recombinant gene product containing the mutant vaccinia virus can be useful for preventing and treating tumors. Examples of tumors, include, without limitations, anal cancer, bile duct cancer, bladder cancer, bone cancer, bowel cancer (colon cancer, rectal cancer), brain cancer, breast cancer, carcinoid cancer, cervix cancer, endocrine cancer, eye cancer, gall bladder cancer, head and neck cancer, Kaposi's sarcoma cancer, kidney cancer, larynx cancer, leukemia, liver cancer, lung cancer, lymphoma cancer, melanoma cancer, mesothelioma cancer, myeloma cancer, neuroendocrine cancer, oesophagus cancer, ovary cancer, pancreas cancer, penis cancer, prostate cancer, skin cancer, soft tissue sarcomas cancer, spinal cord cancer, stomach cancer, testes cancer, thyroid cancer, vagina cancer, vulva cancer, or uterus cancer.

EXAMPLES

The following Examples are set forth to aid in the understanding of the present disclosure, and should not be construed to limit in any way the scope of the invention as defined in the claims contained herein.

Example 1. Virus Isolation and Characterization

Vaccinia virus (strain TianTan) was obtained from the China Center for Type Culture Collection (Wuhan, Hubei) and monkey kidney BSC-40 cells were obtained from the American Type Culture Collection (Manassas, Va.). The cells and virus were cultured in modified Eagle's medium (MEM, Gibco) supplemented with 5% fetal bovine serum, 1% nonessential amino acids, 1% L-glutamine, and 1% antibiotic at 37° C. in a 5% CO2 atmosphere.

24 virus clones from a stock of VACV strain TianTan were randomly selected and plaque purified on BSC-40 cells. Each of the plaque-purified viruses were cultured using BSC-40 cells at a low multiplicity of infection (MOI=0.01) for two days, fixed, stained with crystal violet, and photographed. ImageJ (Schneider et al. Nat. Methods 9 (2012): 671-5) was then used to measure the area sizes of 20 plaques for each virus clone, the plaques were randomly selected from each dish. These viruses produced two kinds of plaques. As shown in FIG. 1, viruses of the more abundant (21/24 clones) TP03 type (representative clones: TP03, TP11, TP12) formed smaller plaques with an area size about half that of viruses of the TP05 type (3/24 clones) (representative clones: TP05, TP13, TP18). The results of virus isolation suggested that the virus stock contained at least two variant forms of viruses, i.e. the TP03 type and the TP05 type.

The titers of TP03 and TP05 were also plotted over time by infecting BSC-40 cells with TP03 and TP05 at MOI=0.01. The viruses were incubated at 37° C., harvested by freeze-thaw, and the yield of virus at each time point was determined by titration on BSC-40 cells. As shown in FIG.

2, the titers of TP03 at each time point is lower than the titers of TP05, indicating that the growth rate of TP03 is slower than that of TP05.

Example 2. Analysis of the 5.7 Kbp Deletions in the TP03 Type Virus

The DNA materials of the TP03 type and the TP05 type were purified and sequenced. According to the sequencing results, the TP03 type is different from the TP05 type by two 5.7 kbp deletions located in the left and right telomeric inverted repeats (TIRs) of the TP03 type virus, respectively.

Figure 3:
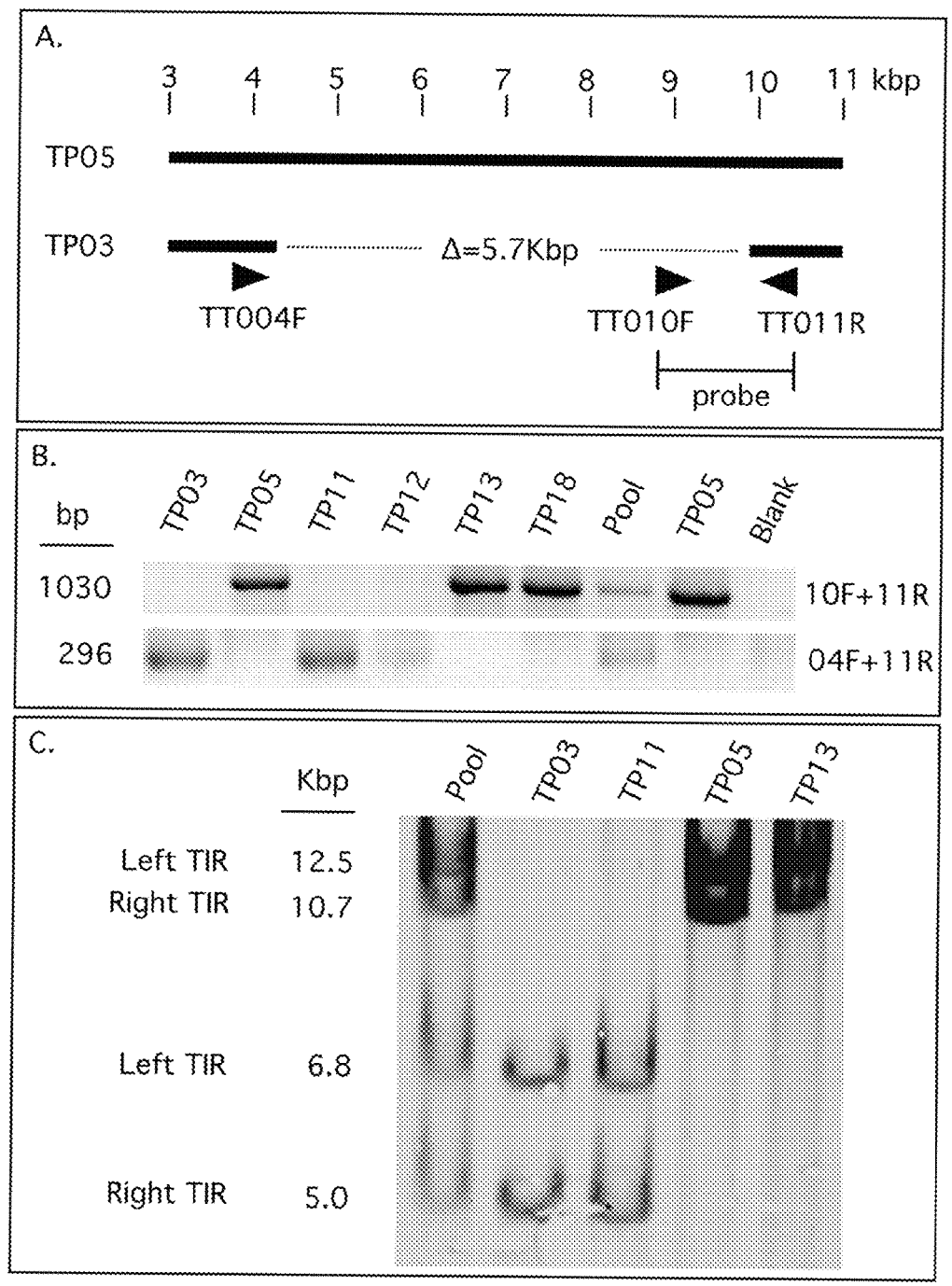
FIG. 3 shows PCR and Southern blot results for confirming the presence of telomeric deletions. The TT004F (SEQ ID NO:1), TT011R (SEQ ID NO:2) and TT010F (SEQ ID NO:3) were used as primers for the PCR.

The presence of the 5.7 kbp deletions in the TIRs of TP03 type was confirmed by PCR. Results of PCR are shown in FIG. 3, in which FIG. 3A shows the binding sites of primers used in PCR (TT004F, TT010F and TT011R) in a map of left telomeres of TP03 and TP05. When the forward primer TT010F (5' TTTTTGTAGGAAGGAGGC 3' (SEQ ID NO:3)) and the reverse primer TT011R (5' CCGGGA-GATGGGATATATGA 3' (SEQ ID NO:2)) were used in PCR, no DNA amplification of TP03 type (TP03, TP11, TP12) was observed (FIG. 3B), which is due to the binding site of primer TT010F is eliminated due to the 5.7 kbp deletions in TP03 type. When the forward primer TT004F (5' TGGATGGCCGTATTGATT 3' (SEQ ID NO:1)) and the reverse primer TT011R were used in PCR, DNA amplification of TP03 type were observed (FIG. 3B).

In contrast, when TT010F and TT011R were used as the primer pair in PCR, DNA amplification of TP05 type were observed (FIG. 3B), this is because the binding site of primer TT010F is retained in the TP05 type. When TT004F and TT011R were used as the primer pair in PCR, no DNA amplification of TP05 type was observed (FIG. 3B) because the distance between the primer pair in TP05 type is too far apart to allow the primers to serve as PCR primers. The 5.7 kbp deletions in TP03 type was also confirmed by Southern blot, in which virus DNAs were digested with ScaI, followed by fractionated on a 0.7% agarose gel, transferred to nylon membranes, and blotted with a biotin-labeled probe. The Southern blot results of ScaI digested DNAs of TP03 type (TP03, TP11), TP05 type (TP05, TP13) and the pool are shown in FIG. 3C. The probe used in the Southern blot encodes DNAs spanning the right side of the deletion boundary (FIG. 3A), thus the 5.7 kb deletions in TP03 type greatly shorten the ScaI fragments encoding the left and right TIRs compared with TP05 type. The unpurified stock of viruses (pool in FIG. 3C) was shown to contain viruses of both TP03 type and TP05 type (FIG. 3C).

Example 3. Virus Genomic Analysis

The gene sequences of various vaccinia viruses are compared with one another to check for sequence similarity or differences. The vaccinia virus strains analyzed include CL3, ACAM2K, RPXV, Duke, Lister, CVA, Cop, WR, HPXV and TianTan (TP03 and TP05). "TP00" refers to the previously published TianTan virus sequence (AF095689).

Genome assemblies were prepared using CLC Genomics Workbench (v4.6) and annotated using GATU (Tcherepanov et al. BMC Genomics 7 (2006): 150) as described previously (Qin et al. J. Virol. 85 (2011): 13049-60). Bioinformatic analyses were performed using Viral Genome Organizer (Lefkowitz et al. Nucleic Acids Res. 33 (2005): D311-6; Upton et al. Virus Res. 70 (2000): 55-64) and Poxvirus Orthologous Clusters (Ehlers et al. Bioinformatics 18 (2002): 1544-5). These and additional bioinformatics tools can be accessed at www.virology.ca. An alignment of virus sequences lying between the gene homologs of genes DVX058 to DVX155 (VACV Copenhagen genes F9L-to-A24R) for the indicated viruses were prepared.

Figure 4:
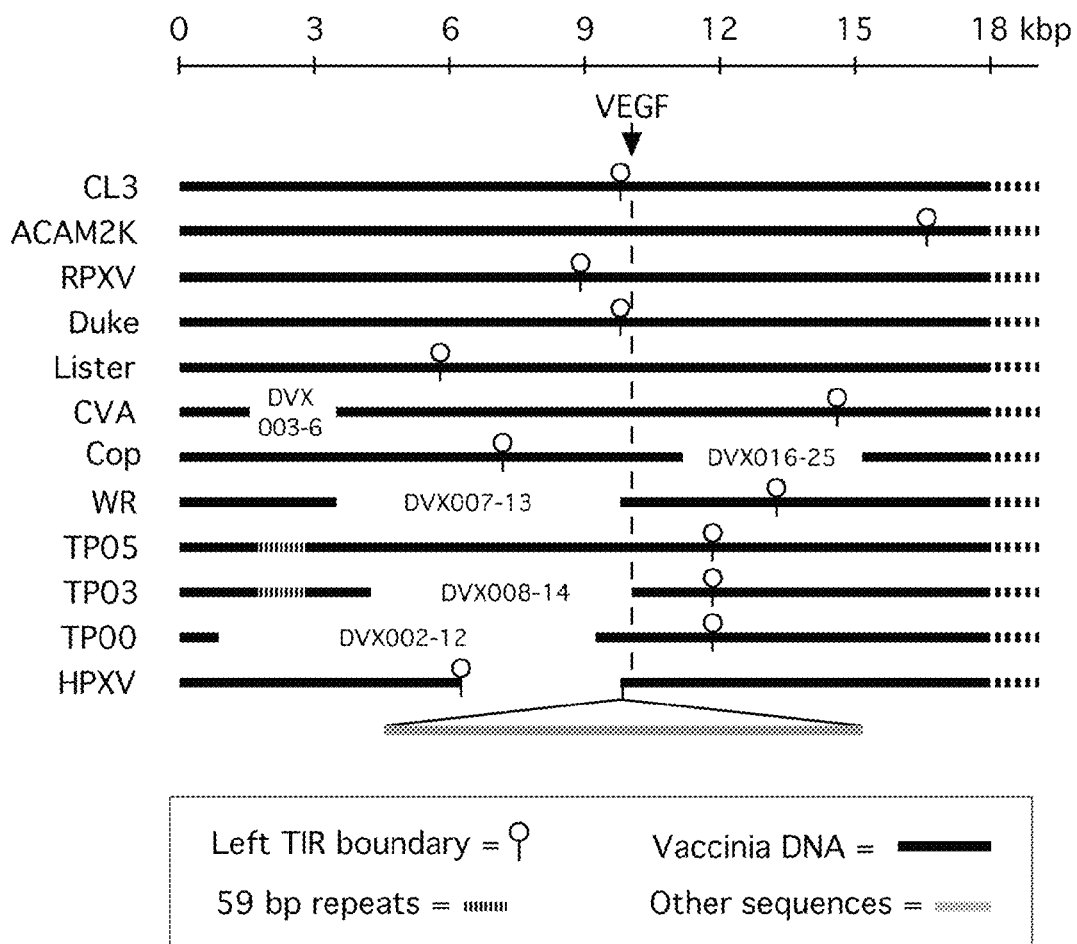
FIG. 4 shows a comparison of the locations of gene deletions in the left telomere regions of 12 common VACV strains. The circled vertical bars represent left TIR boundary. TP03 includes a deletion that extends into the VGF genes in the left telomere region of the virus genome.

BLASTN search was run using ~20 kbp of sequence spanning the left telomere of common vaccinia virus strains (FIG. 4). The location of left TIR boundary (circled vertical bars in FIG. 4) varies between the strains due to the presence of different deletions in the region surrounding the left TIR boundary. TP05 resembles more complete VACV strains, and the TIRs of TP05 most closely resemble those of other VACV strains.

Figure 5:
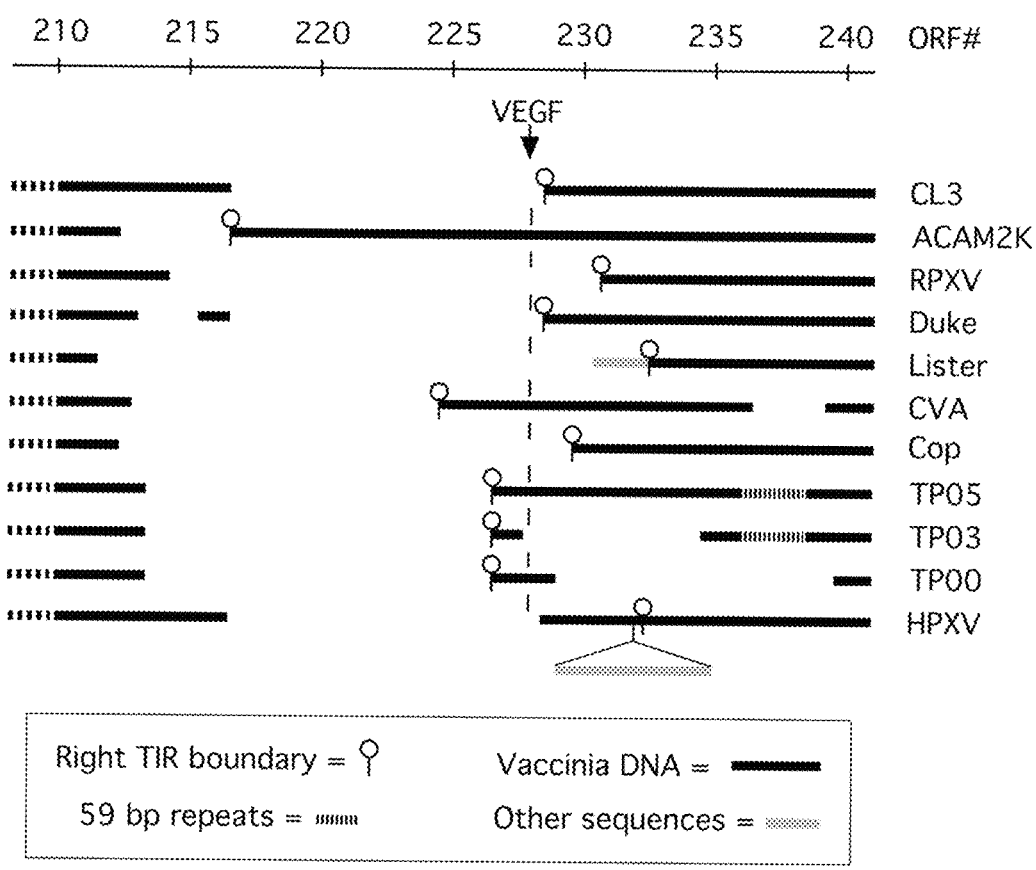
FIG. 5 shows a comparison of the locations of gene deletions in the right telomere regions of 12 common VACV strains. The circled vertical bars represent the right TIR boundary. TP03 includes a deletion that extends into the VGF genes in the right telomere region of the virus genome.

A similar pattern of gene deletions is also found in the right telomere of the different VACV genomes (FIG. 5). The TP05 strain encodes a complement of genes in the right telomere similar to most other VACV strains, while TP03 encodes a unique deletion at the right of the TIR boundary (barred circle in FIG. 5) that extends into VGF gene compared with other VACV strains.

Genes located in the symmetrical 5.7 kbp deletion of TP03 type virus are compared with the homolog genes of the TP05 type virus and the Copenhagen strain. As shown in the table in FIG. 6, in comparison with TP05 and the Copenhagen strain, the TP03 type virus has the Serpin gene (SPI-1), Ankyrin gene and several other genes completely removed from the TIRs on both ends of the virus genome. In addition, the promoter and N-terminal region of the VGF gene is also removed from both ends of the TP03 DNA, only a 253 bp C-terminal region of the VGF gene is left on each end of the TP03 DNA.

What is claimed is:

1. A mutant vaccinia virus strain which is capable of selectively replicating in tumor cells, and decreasing virulence to normal cells, wherein the encoding sequences of two vaccinia virus growth factor (VGF) genes, Serpin gene, and Ankyrin gene in the genome of the virus are completely or partially truncated so that the virus cannot express functionally active VGF proteins, Serpin proteins or Ankyrin proteins, wherein the strain is deposited under the CCTCC deposit number of V201307.

2. The mutant vaccinia virus strain of claim 1, wherein the strain produces plaques smaller than the corresponding non-mutant vaccinia virus.

3. The mutant vaccinia virus strain of claim 1, wherein the tumor cells are selected from the group consisting of Hepal-6, MCF-7, TCa8113, ACC-M, LNCaP, HEK293, Hep3B, A549, 7402, 7721, and Hela cells.

4. A method for selectively delivering and expressing a target gene in a tumor cell, comprising the steps of inserting a target gene into the genome of the mutant vaccinia virus of claim 1 to prepare a vector, and delivering the vector in a tumor cell.

5. A method for producing a recombinant gene product, comprising inserting a target gene into the genome of the mutant vaccinia virus of claim 1.

6. A recombinant gene product comprising a nucleic acid sequence of the mutant vaccinia virus of claim 1 and a nucleic acid sequence of a target gene.

7. A method for lowering multiplicity of infection of a vaccinia virus in normal cells while maintaining selective replication in tumor cells, comprising:
completely or partially truncating the encoding sequences of two vaccinia virus growth factor (VGF) genes, Serpin gene, and Ankyrin gene in the genome of the vaccinia virus, whereby the vaccinia virus cannot express functionally active VGF proteins, Serpin proteins and Ankyrin proteins, wherein the strain is deposited under the CCTCC deposit number of V201307.

* * * * *

SEQUENCE LISTING

<160> NUMBER OF SEQ ID NOS: 3

<210> SEQ ID NO 1
<211> LENGTH: 18
<212> TYPE: DNA
<213> ORGANISM: Artificial Sequence
<220> FEATURE:
<223> OTHER INFORMATION: TT004F, forward primer

<400> SEQUENCE: 1
tggatggccg tattgatt                                        18

<210> SEQ ID NO 2
<211> LENGTH: 20
<212> TYPE: DNA

```
<213> ORGANISM: Artificial Sequence
<220> FEATURE:
<223> OTHER INFORMATION: TT011R, reverse primer

<400> SEQUENCE: 2
ccgggagatg ggatatatga                                              20

<210> SEQ ID NO 3
<211> LENGTH: 18
<212> TYPE: DNA
<213> ORGANISM: Artificial Sequence
<220> FEATURE:
<223> OTHER INFORMATION: TT010F, forward primer

<400> SEQUENCE: 3
tttttgtagg aaggaggc                                                18
```